(12) United States Patent
Van Hanja et al.

(10) Patent No.: US 7,642,424 B2
(45) Date of Patent: Jan. 5, 2010

(54) TALL FESCUE ENDOPHYTE E34

(75) Inventors: Nicolas Van Hanja, Mas Grenier (FR); Jacobus de Bruijn, Mas Grenier (FR)

(73) Assignee: Barenbrug USA, Inc., Tangent, OR (US)

( * ) Notice: Subject to any disclaimer, the term of this patent is extended or adjusted under 35 U.S.C. 154(b) by 1 day.

(21) Appl. No.: 11/775,702

(22) Filed: Jul. 10, 2007

(65) Prior Publication Data

US 2008/0022420 A1      Jan. 24, 2008

Related U.S. Application Data

(60) Provisional application No. 60/806,859, filed on Jul. 10, 2006.

(51) Int. Cl.
*A01H 5/00* (2006.01)
*A01H 5/10* (2006.01)
*A01H 15/00* (2006.01)

(52) U.S. Cl. .................... 800/320; 800/298; 435/254.1; 424/93.5

(58) Field of Classification Search .................. 800/298, 800/320, 265; 435/254.1; 424/95.3
See application file for complete search history.

(56) References Cited

U.S. PATENT DOCUMENTS

| 5,723,720 | A | 3/1998 | Brede et al. |
| 6,072,107 | A * | 6/2000 | Latch et al. ................. 800/320 |
| 6,111,170 | A | 8/2000 | Latch et al. |
| 6,335,188 | B1 * | 1/2002 | Schardl et al. ............. 435/193 |
| 6,677,507 | B2 * | 1/2004 | de Bruijn ................... 800/320 |
| 6,815,591 | B1 | 11/2004 | Hignight et al. |
| 2004/0143875 | A1 | 7/2004 | de Bruijn |

FOREIGN PATENT DOCUMENTS

WO    WO 2004/029227 A1    4/2004

OTHER PUBLICATIONS

Christensen Variation in the ability of *Acremonium* endophytes of *Lelium perenne Festuca arundinacea* and *F Pratensis* to form compatible associations in the three grasses. Mycol. Res 99(4) 466-470 1995.*

* cited by examiner

*Primary Examiner*—Annette H Para
(74) *Attorney, Agent, or Firm*—Klarquist Sparkman, LLP (57) ABSTRACT

A tall fescue variety known as BE9301A which is inoculated with endophyte E34 is provided. Also provided is the endophyte E34. Methods of using the grass plant, seed, and endophyte are also provided. In particular examples, BE9301A is suitable for use in forage pastures due to the low amounts of alkaloids present.

37 Claims, 3 Drawing Sheets

Fig. 2 Genotypic data of the different endophyte isolates for five SSR loci.

| Strain(s) | Putative species | Data source | Allele size (bp) | | | | |
|---|---|---|---|---|---|---|---|
| | | | B4 | B6 | B9 | B10 | B11 |
| ArkPlus | | DPI | 100.2 & 103.9[c] (98.2 & 101.9)[d] | 193.8[d] | 272.0[d] | 163.1 & 166.0 & 172.1[c] (162.1, 165.0 & 171.1)[d] | 165.4 & 193.0[c] (164.4 & 192.0)[d] |
| | N. coenophialum | Latch et al. (2000)[a] | 100.0 & 102.4 | 193.7 | 271.9 | 163.5, 172.1 & 180.8 | 149.8 & 192.7 |
| BE 9301 | N. coenophialum | DPI[b] | 100.3 & 104.0[c] (98.3 & 102.0)[d] | 193.9[d] | 272.0[d] | 163.3, 172.1[e] & 180.5[c] (162.3, 171.1[e] & 179.5)[d] | 149.6 & 188.9[c] (148.6 & 187.9)[d] |
| Lp19 | N. lolii | Moon et al. (1999)[a] | 100.0 | 187.6 | 247.4 | 178.0 | 180.8 |
| | | DPI[b] | 100.3[c] (98.3)[d] | 187.5[d] | 246.9[d] | 177.9[c] (176.9)[d] | 181.1[c] (180.1)[d] |

[a] Data generated on ABI Prism 377 DNA sequencer
[b] Data generated on MegaBACE 4000 platform
[c] Data amended according to allele size discrepancies detected between genotyping platforms in strains Lp19 an AR1
[d] Raw data
[e] Allele not consistently detected across multiple analyses.

TALL FESCUE ENDOPHYTE E34

CROSS REFERENCE TO RELATED APPLICATION

This application claims priority from U.S. provisional application No. 60/806,859, filed Jul. 10, 2006, which is herein incorporated by reference in its entirety.

FIELD

This disclosure relates to a new tall fescue grass with an endophyte that is more palatable and late maturing compared to other known tall fescues, as well as to other known endophytes used to inoculate the grass. One example of this grass is known as breeder's code BE9301A and the endophyte is known as E34.

BACKGROUND

The majority of the grass forage pastures in the United States are located in regions that are subjected to extreme climatic conditions with hot, dry summers and very cold winters with no snow cover. The predominant cool season perennial grass grown in the Southeast United States and transition zone is tall fescue (*Festuca arundinacea*).

Summer survival of tall fescue is related to presence of living fungal endophyte (*Neotyphodium coenophialum*) in the plants. For example, the presence of endophyte in tall fescue as well as perennial ryegrass can enhance drought tolerance, summer survival, insect tolerance and disease tolerance. However, cattle grazing forage from most endophyte-infected tall fescue cultivars suffer from fescue toxicosis. Fescue toxicosis results from ingesting ergot alkaloids. Ergovaline is considered to be the main ergot alkaloid responsible for most animal problems.

Therefore, new endophytes and forage grasses containing endophytes are needed, such as those that have a less toxic effect on grazing animals.

SUMMARY

Herein disclosed is a *Neotyphodium* endophyte (E34) used to inoculate the disclosed BE9301A grass plants and seeds. In a particular example, the endophyte is present in an axenic culture of an endophyte deposited with Centraalbureau voor Schimmelcultures, P.O. Box 85167, 3508 AD Utrecht, The Netherlands (Deposit No. CBS 119998) on Jun. 27, 2006 under the Budapest Treaty. This endophyte will be irrevocably and without restriction released to the public upon the issuance of a patent. Therefore, this endophyte is known and readily available to the public. In one example, the disclosure provides endophyte deposited as Centraalbureau voor Schimmelcultures Deposit No: CBS 119998. This endophyte can be used to form symbiotic host relationships with grass plants and is different from all known endophytes.

Also disclosed herein is a tall fescue variety known as breeder's code BE9301A that contains the endophyte (E34) and is different from all known varieties of tall fescue plants. In one example, mature BE9301A plants have a late maturing date (such as early May, for example May 2), reach a height from about 128 cm to about 137 cm tall, have a high rust tolerance, have a high bacterial wilt tolerance, and/or have a high forage yields and persistence. BE9301A tall fescue plant leaves are softer than other tall fescues having endophytes. In some examples, BE9301A plants have increased persistence and acceptance by cattle compared to other tall fescues, such as other tall fescues having endophytes.

At least 2500 seeds of BE9301A were deposited with The American Type Culture Collection (ATCC, Manassas, Va.; ATCC Deposit No. PTA-7709) on Jul. 11, 2006 under the Budapest Treaty. These seeds will be irrevocably and without restriction released to the public upon the issuance of a patent. Therefore, these seeds are known and readily available to the public. In one example, the disclosure provides grass seed deposited as ATCC No: PTA-7709.

DETAILED DESCRIPTION OF SEVERAL EMBODIMENTS

In one example, the disclosure provides tall fescue plants including the morphological and physiological characteristics of BE9301A. In another example, the disclosure provides tall fescue plants having all of the morphological and physiological characteristics of BE9301A. Also disclosed are seeds of such plants, progeny of such plants, and vegetative sprigs or clones of such plants. In another example, the disclosure provides grass plants having the genotype of BE9301A.

The disclosure also encompasses tall fescue plants that are produced by crossing BE9301A with other grass varieties (out-crossing). Seeds and plants generated from those seeds that are the result of a first out-crossing are referred to as an F1 generation (first generation). Any grass variety capable of crossing with BE9301 can be used to create and out-cross, including fescue varieties or rye grass varieties. In some examples the BE9301A is crossed with one of the varieties described in the examples section. Accordingly, the disclosure also provides seeds resulting from such out-cross, grass plants grown from such seeds, and vegetative sprigs or clones from such a cross. In one example, the seeds resulting from the cross are part of a seed mixture.

The disclosure also encompasses tall fescue plants that are produced by self-crossing BE9301A. Self-crossing as used herein describes the process of letting the same BE9301A plant pollinate itself, or letting two BE9301A plants pollinate each other. Such self-crossing produces more BE9301A seeds and plants. Accordingly, the disclosure provides seeds resulting from such self-cross, grass plants grown from such seeds, and vegetative sprigs or clones from such a cross. In one example, the seeds resulting from the cross are part of a seed mixture.

One of ordinary skill in the art readily understands that seed mixtures are desired in many circumstances. Seed mixtures are used to increase the amount of grass that grows in a certain location, such as in a pasture. Generally, the mixture is designed to contain more than one variety of grass seed or grass variety of other grass species so that if the weather conditions vary at least one of the included varieties performs well. Seed mixtures include not only BE9301A seeds, seeds from self-crossing BE9301A, or F1 seeds from out-crossing BE9301A in combination of any other known grass seed, such as other known tall fescue seeds. For example, BE9301A seeds can be combined with one or more of the varieties described herein.

In another example, the disclosure provides a method of producing grass seed, including planting seed from BE9301A under conditions that result in the germination of the seed, growth of grass plants and setting of progeny seed, and then harvesting the progeny seed. Also disclosed is grass seed produced by this method, as well as grass seed mixtures including such grass seed.

Also disclosed is a method of producing a grass plant which includes crossing a grass plant produced from BE9301A with at least one other grass plant to produce at least one seed, harvesting the seed, and germinating the seed to produce at least one progeny grass plant. Included in the disclosure are grass plants produced using this method, as well as a vegetative sprig or clone of the grass plant.

The grass plants disclosed herein can be planted in a variety of areas, for example in areas where grazing of farm animals is desired. Examples include, but are not limited to pastures, such as areas for animal grazing.

The disclosure also includes sward or animal feed, such as hay, which includes the grass plants (such as BE9301A plants) disclosed herein. The sward can be planted in any area where grass plants are desired, such as a pasture.

In one example, the grass plants disclosed herein include one or more transgenes.

In some examples, the disclosed endophyte, (*Neotyphodium* endophyte E34), can form a stable synthetic combination with a grass host, such as a tall fescue (*Festuca arundinacea*) or a perennial ryegrass (*Lolium perenne*). In a particular example, the grass is a temperate tall fescue cultivar. Exemplary tall fescue cultivars include Dovey, Drover, Prosper, Barcarella, BAR FA 6FRD, Barcel, Barolex, BarElite, and Bariane, and exemplary perennial ryegrasses include Barsprinter and Remington.

A "synthetic endophyte/grass combination" is the combination of an endophyte and a grass cultivar (such as a tall fescue or perennial ryegrass or other forage variety) each of which has been isolated from nature, but the combination of which does not exist in nature. For example, the grass cultivar can be a culturally improved grass variety, such as having one or more desirable characteristics, such as increased persistence, drought tolerance, resistance to one or more diseases, and the like. Methods of making such a synthetic combination are known in the art, and can include inoculating the desired grass cultivar (such as a tall fescue cultivar) with an axenic culture of endophyte E34, or crossing a synthetic endophyte/grass cultivar combination with an endophyte-free grass cultivar (such as a tall fescue cultivar or a perennial ryegrass cultivar) to form a new cultivar infected with the endophyte. In one example, the endophyte-free grass cultivar includes one or more desirable characteristics, such as disease resistance, drought resistance, persistence, low toxicity to grazing animals, and so forth.

In particular examples, the disclosed combinations provide a grass plant having reduced amounts of one or more alkaloids compared to naturally occurring endophyte/grass combinations, reduced toxicity to livestock compared to naturally occurring endophyte/grass combinations, improved palatability and digestibility compared to naturally occurring endophyte/grass combinations, or combinations thereof. In a specific example, the axenic culture of endophyte E34 in synthetic combination with a tall fescue cultivar, such as the synthetic combination of BE9301A, produces levels of ergovaline of less than 100 ppb (for example less than 50 ppb, such as 100-10 ppb or 50-20 ppb), such as about 38 ppb compared to 524 ppb produced by Kentucky 31 (containing another natural toxic endophyte). In another specific example, the axenic culture of endophyte E34 in synthetic combination with a tall fescue cultivar, such as the synthetic combination of BE9301A, produces levels of ergot alkaloid of less than 500 ppb (for example less than 250 ppb, such as 500-100 ppb or 250-70 ppb), such as about 122 ppb of ergot alkaloid compared to 1369 ppb (numbers are the average of those shown in Table 7) produced by Kentucky 31 (containing another natural toxic endophyte).

Also provided by the present disclosure are seeds of the disclosed synthetic combinations. For example, such seeds can be harvested from grass plants (such as tall fescue or perennial ryegrass plants inoculated with the disclosed endophyte. In another example, the seeds are harvested from plants of the disclosed synthetic endophyte/grass combination grown from seeds harvested from grass plants inoculated with the endophyte.

The following examples are provided to better describe the present disclosure and to guide those of ordinary skill in the art in the practice of the present disclosure. The singular forms "a," "an," and "the" refer to one or more than one, unless the context clearly dictates otherwise. For example, the term "comprising a grass plant" includes single or plural plants and is considered equivalent to the phrase "comprising at least one grass plant." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs.

The foregoing and other objects and features of the disclosure will become more apparent from the following detailed description of several embodiments.

EXAMPLE 1

Endophyte Isolation and Inoculation of Barcel

This example describes methods used to isolate the E34 endophyte and to inoculate the Barcel variety with the E34 endophyte.

The Barcel variety of tall fescue (US Plant Variety Protection 8100085 issued Jul. 15, 1982) was developed by Barenbrug Research in Wolfheze, The Netherlands.

The endophyte E34 was isolated from its natural host, a tall fescue ecotype. Seeds of various different grasses were analyzed for ergovaline alkaloid. Endophyte was isolated from seeds producing significantly low ergovaline content compared to Kentucky 31 tall fescue seeds.

The E34 endophyte was isolated from seed as follows. Seeds (3 g) were sterilized in 5% NaHCl with 2 drops 'Tween 20' for 2 hours, and then rinsed with water. This was repeated, with a final rinsing in a laminar flow hood with sterile water. Approximately 50 seeds were placed into an empty Petri dish under sterile conditions. The outer coats of the seeds were removed, then the embryos were removed and suspended in sterile water (to keep moist). Each embryo was cut in half longitudinally to prevent germination, and placed into a bottle containing Mirashige & Skoog media containing 2,4:D media. The bottles were placed on an orbital shaker at 100 rpm in the dark at 20° C. for 4 weeks, until the first fungus was visible. Balls of fungus were removed from the liquid media, and plated on PDA media. If fungus balls were not visible, the contents of the bottle were poured onto a Petri dish, and then the liquid was decanted off (allowing any fungus present to remain on the plate).

The E34 endophyte strain does not sporulate and is not fast growing. The color of the colony was white/brown. The aerial mycelium was felted and the texture was dry.

Isolated endophytes were further inoculated in developed cultivars such as Barcel and other forage grasses. The methods used for inoculation were as follows. Seeds (3 g) were sterilized in 5% NaHCl with 2 drops 'Tween 20' for 2 hours. The seeds were then rinsed with water overnight. The following day, excess water was removed and the sterilization was repeated for 2 hours, subsequently the seed were rinsed thoroughly in laminar flow with sterile water. The sterile seeds (10) were placed in a circle in a Petri dish containing 1.5% water agar, and incubated at 20° C. or 25° C., and allowed to grow until the shoot began to emerge from coleoptile. Seedlings in the Petri dish were inoculated with fresh endophyte (transferred to fresh media up to fourteen days before inoculation) under sterile conditions. A small piece of endophyte mycelium (about 0.5 mm) was removed with needle or forceps. The base of the shoot was pierced with a needle to generate a hole, and the endophyte mycelium piece placed into the hole. Ideally, the endophyte was positioned in the center of the shoot.

The inoculated seedlings were incubated at 20° C. for 7 days (12 hrs light), then transferred to test tubes or soil. Test tube transfer was as follows. Inoculated seedlings were removed from the Petri dish and placed into test tubes containing solid M&S media under sterile conditions. Tubes were incubated at 20° C. (16 hrs light) for 8 weeks. Subsequently, presence of the endophyte was screened, and those having endophyte transplanted into soil. Inoculated seedlings were removed from the Petri dish or the test tube and placed into a seed tray with potting mix. Root and seed were covered, leaving most of the shoot exposed. The shoot was cut to about 10 cm, and the seedlings were watered and covered to prevent evaporation. Seedlings were incubated at 20° C. for 2 weeks (from test tube or Petri dish), then placed in a glasshouse. Seedlings were trimmed to encourage tiller multiplication. After 8 weeks (when more than one tiller is present per plant) plants were screened for the presence endophyte.

Out of 44 seedlings of Barcel that were inoculated, 7 seedlings that tested positive for endophyte were planted in a field at Barenbrug Tourneur Recherches, Mas Grenier, France. Seeds from these plants were harvested. The harvested seed was tested for endophyte for verification that inoculated endophyte was stable. Five plants with desirable forage attributes (such as soft leafiness, late maturity, and freedom from diseases) and presence of endophyte were chosen. The seeds from these five were harvested separately. The seed was tested for the presence of endophyte. 100% of the seeds were positive for endophyte. These seeds were coded as BE9399.

BE 9399 seed was used to grow 800 plants in a greenhouse. Four rows of 200 plants each were transplanted between alternating rows of two other improved tall fescue varieties (BAR 3FA BTR9 and BAR FA 1BTR10). These two other tall fescue varieties are also developed for late maturity, and high palatability and digestibility and used as pollen source for crossing with BE9399 plants. In the field growing plants of BE9399 endophyte presence were rechecked at two times.

After pollination, the BAR 3FABTR9 and BAR FA 1BTR10 were removed and seeds from only the four rows of BE9399 plants was harvested. This harvested seed was coded as BE9301. The harvested seed tested 80% positive for endophyte. In the fall, BE9301 seed was grown in greenhouse and 2110 live seedlings were analyzed for endophyte and 1650 seedlings tested positive for endophyte and were transplanted in a multiplication block in field. In spring, the multiplication block was checked for uniformity. In summer, the seed was harvested from this block was coded as BE9301A and had 100% endophyte.

BE9301A seed has been used for forage trials and further multiplication in U.S. and France. The BE9301A variety retains endophyte viability and transfer through at least three generations.

Detection of Endophyte

Endophyte was detected in grass seed as follows. Seeds were incubated in a 5% NaOH solution overnight then rinsed with water. Seeds were placed on a glass slide and a drop of analine blue (0.325 g aniline blue, 100 ml water, 50 ml lactic acid 85%) was added. The seed was crushed with steady pressure applied to a cover slip on top of the seed. Hyphae are stained blue and located mostly in the area of the darkly stained aleurone cells, indicating the presence of endophyte.

Endophyte was detected in grass plants as follows. A tiller from the plant was removed, and all dead leaves removed. The root was trimmed, leaving 0-5 cm above the ground, close to the meristem, were the mycelium density is the highest. A longitudinal section from the adaxial surface of the leaf sheath was removed. The epidermal strip with the inner surface facing upwards was placed onto a glass slide containing a drop of aniline blue. The sample was examined for the presence of characteristic intercellular mycelium as described above.

EXAMPLE 2

Seed Deposits

Seeds of the tall fescue variety BE9301A inoculated with endophyte described in Example 1 were deposited with the ATCC (Manassas, Va.) under the Budapest Treaty on Jul. 11, 2006 under accession number PTA-7709. The identification reference by the depositor is BAR FA BE9301A. The variety is also maintained at, and available from, Barenbrug U.S.A., Inc., P.O. Box 239, Tangent, Oreg. 97389.

EXAMPLE 3

Endophyte Deposit

The endophyte described in Example 1 was deposited with the Centraalbureau voor Schimmelcultures depository in The Netherlands under the Budapest Treaty on Jun. 27, 2006 under Deposit No. CBS 119998. The endophyte is also maintained at, and available from, Barenbrug Holland, Stationstraat 40, Post bus 4, 6678 ZG Oosterhout, The Netherlands.

EXAMPLE 4

Analysis of Endophyte by Polymorphic DNA Microsatellite Analysis

This example describes methods used to genetically analyze E34 and the commercial isolates, such as ArkPlus. The results from the genetic analysis indicate that E34 is genetically diverse from ArkPlus. E-34 was also identified as a member of the taxon *N. coenophialum*.

Figure 2:
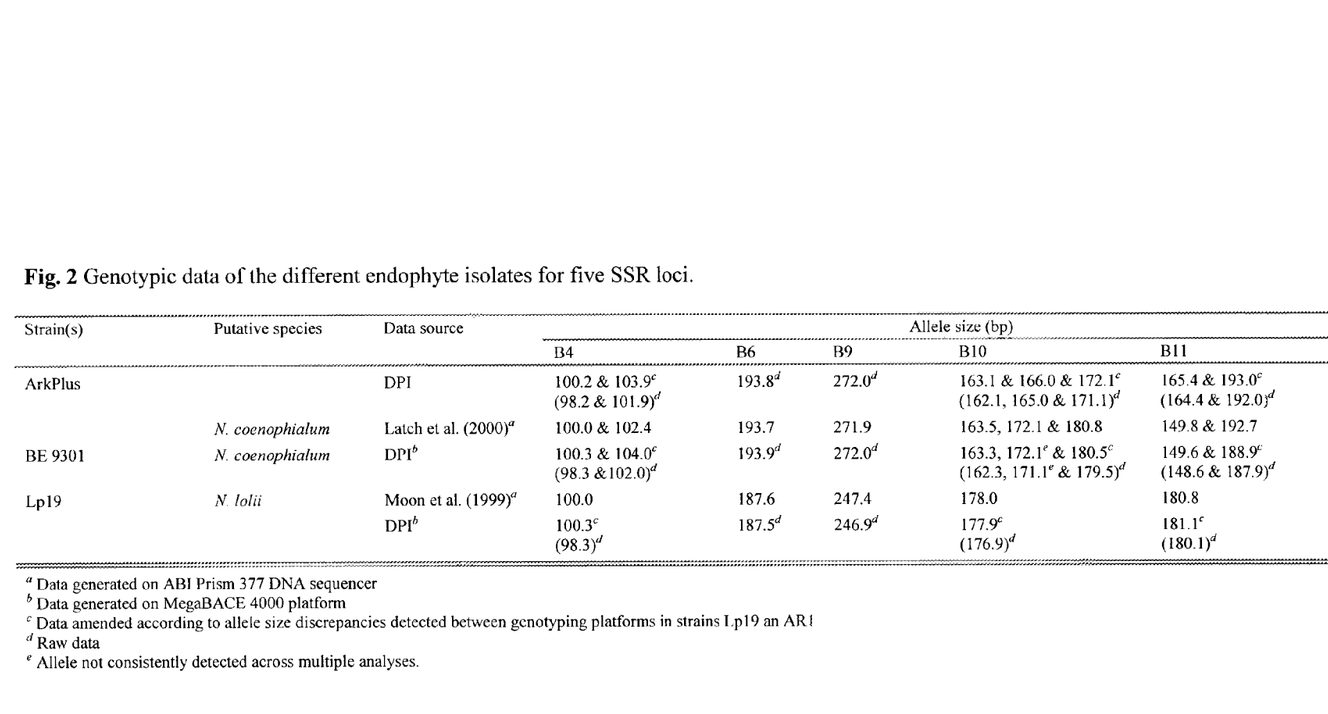
FIG. 2 is a table showing the allele sizes produced using the markers identified in the table.

Genetic differences (either in allele size or number of alleles) were detected between isolate E34 and an isolate of ArkPlus for more than 18 of the 39 SSR loci (see, FIG. 2 which provides allele size information). This includes two of the five SSR loci described in U.S. Pat. No. 6,111,170 herein incorporated by reference.

Materials and Methods

To obtain mycelia for genomic DNA extraction, the isolates were grown in 2.4% w/v potato dextrose broth (Difco, Sparks, Md., USA) at 22° C. in the dark with shaking at 150 rpm for 2-3 weeks. Total genomic DNA was extracted from lyophilised mycelia from each isolate following the method of Möller et al. (*Nucleic Acids Research.* 20:6115-6116, 1997).

Total genomic DNA was extracted from either single seeds or seed bulks (5 or 10 seeds) using the Plant DNeasy kit (Qiagen, Hilden, Germany).

The E34 isolate as well as two *N. lolii* isolates (Lp19 and AR1) were genetically characterised with a total of 39 SSR markers (Table 1). Polymerase chain reaction (PCR) amplifications were performed using the markers and methods described in U.S. Pat. No. 6,111,170 (B4, B6, B9, B10 and B11), however, the error in primer B11.4 was corrected using the sequence described in Moon et al., *Applied and Environmental Microbiology* 65:1268-1279, 1999. For the remaining markers, PCR amplifications were performed in 20 µl reaction volumes containing 1× PCR buffer (Bioline, London, UK), 0.2 mM of each dNTP (GE Healthcare, Chalfont St Giles, UK), 0.5 U Immolase (Bioline), 0.25 µM each primer (Sigma Aldrich, St. Louis, Mo., USA; Applied Biosystems, Foster City, Calif.) and 10 ng genomic DNA. The forward primer was 5'-end labelled with a fluorescent phosphoramidite dye (6-FAM, HEX or NED). Amplification was performed in a thermocycler (GeneAmp, PE Applied Biosystems, Foster City, Calif., USA) using an appropriate touchdown profile depending on the $T_m$ value of the primer pairs: (1) 10 minutes at 95° C., 10 cycles of 30 seconds at 94° C., 30 seconds at 65° C., 1 minute at 72° C. with a reduction of annealing temperature of 1° C. every cycle, followed by 20 cycles of 30 seconds at 94° C., 30 seconds at 55° C., 1 minute at 72° C.; (2) a similar profile as (1) with an initial annealing temperature of 60° C. and final annealing temperature of 50° C.; (3) a similar profile as (1) with an initial annealing temperature of 55° C. and final annealing temperature of 45° C.; and (4) a similar profile as (1) with an initial annealing temperature of 50° C. and final annealing temperature of 40° C. For each isolate, reactions with different sized-products and fluorochrome labels were combined and purified by isopropanol precipitation. Purified products (2 µl) were mixed with MegaBACE loading solution containing internal size standard ET400-R (GE Healthcare) and denatured at 94° C. for 5 minutes before analysis on the MegaBACE 4000 capillary electrophoresis platform (GE Healthcare).

TABLE 1

Endophyte SSR markers.

| Marker | Motif | Touchdown program |
|---|---|---|
| NCESTA1AA09 | $(GAC)_7$ | 2 |
| NCESTA1AG11 | $(CTCAG)_5$ | 1 |
| NCESTA1AG12 | $(GCAC)_6$ | 3 |
| NCESTA1BD09 | $(GAC)_6$ | 1 |
| NCESTA1CC10 | $(GT)_4(GC)_1(GT)_4$ | 1 |
| NCESTA1DH04 | $(GTC)_8$ | 2 |
| NCESTA1FC04 | $(GCAAA)_4$ | 3 |
| NCESTA1FH03 | $(GCC)_7$ | 4 |
| NCESTA1GA07 | $(CAT)_7$ | 4 |
| NCESTA1HA02 | $(CAG)_5$ | 1 |
| NCESTA1IC04 | $(GCA)_4(AG)_1(AAC)_4$ | 2 |
| NCESTA1IG08 | $(GCA)_8$ | 2 |
| NLESTA1BB08 | $(TC)_9$ | 2 |
| NLESTA1CC02 | $(AT)_4(GT)_1(AT)_4(A)_1(AT)_4$ | 1 |
| NLESTA1CC05 | $(TGT)_{17}$ | 1 |
| NLESTA1EE05 | $(GCATC)_6(GTATC)_1(GCATC)_1(GTATC)_1$ | 2 |
| NLESTA1GA07 | $(CT)_5(A)_1(CT)_4$ | 3 |
| NLESTA1GF09 | $(GAC)_4$ | 1 |
| NLESTA1IG04 | $(CAC)_6$ | 1 |
| NLESTA1LB02 | $(ACA)_{12}$ | 2 |
| NLESTA1LB04 | $(CGG)_6$ | 1 |
| NLESTA1LF05 | $(ACA)_4(GCA)_9$ | 1 |
| NLESTA1NB03 | $(CCA)_3(TCA)_1(CCA)_5$ | 1 |
| NLESTA1NF04 | $(TGC)_8(TGA)_3(TGG)_1(TGA)_3$ | 1 |
| NLESTA1NG03 | $(GTC)_6$ | 1 |
| NLESTA1PF06 | $(TA)_7$ | 2 |
| NLESTA1QA09 | $(GA)_{20}(G)_1(GA)_3$ | 3 |
| NLESTA1QE05 | $(GCA)_9$ | 3 |
| NLESTA1RD04 | $(GGA)_4$ | 1 |
| NLESTA1TA10 | $(TC)_{11}$ | 2 |
| NLESTA1XB01 | $(GTG)_4$ | 1 |
| NLESTA1XC06 | $(GAC)_8$ | 2 |
| NCSSRA1AH02 | $(CT)_1(C)_1(CT)_6$ | 2 |
| EFSSRA1AH07 | $(GTT)_{10}(GCT)_1(GTT)_1$ | 2 |
| B4 | $(CA)_3(GCG)_1(CA)_3(ACG)_1(CA)_3(A)_1(CA)_4$ | |
| B6 | $(CAT)_2(CAC)_1(CAT)_3$ | |
| B9 | $(G)_5(AG)_9$ and $(GAGAG)_2(C)_1(GAGGA)_2$ | |
| B10 | $(AGC)_3(CG)_1(CAT)_3(CAA)_5$ | |
| B11 | $(GACA)_{18}$ | |

Products or alleles detected across each of the isolates were characterized by size (i.e. number of base pairs) using MegaBACE Fragment Profiler version 1.2 software (GE Healthcare). Isolates were scored for the presence (1) and absence (0) of each allele for each SSR locus. For seed samples, due to inconsistent detection of multiple alleles, the data score for the various SSR loci was taken from different single and bulk seed samples to ensure all multiple alleles were accounted for. Data matrices were generated and analysed with NTSYS version 2.02i software (Exeter Software, Setaukat, N.Y., USA). Genetic identity between isolates was measured using the simple matching coefficient. Phenograms were constructed from the genetic distances by the unweighted pair group method of arithmetic averages (UPGMA). The goodness of fit of the clustering method was tested by Mantel test statistics comparing the genetic identity matrix with the cophentic matrix.

EXAMPLE 5

Morphological Characteristics of BE9301A

This example describes field trials that were conducted to compare morphological characteristics of the BE9301A variety to other tall fescue grass varieties.

Seeds from fourteen different tall fescue varieties were sown in greenhouse potting medium in August 2003. After germination, the seedlings were transplanted into plug trays in September 2003. Seedlings were grown in the greenhouse until the plugs were filled with roots. During December 2003, the plug seedlings were transplanted in a field nursery near Albany, Oreg. The seedlings were transplanted two feet apart. Sixty seedlings from each variety were grown in this field nursery. The field nursery was maintained with crop management practices used for grass seed production systems in the region.

In mid July 2004 and 2005, the following morphological characteristics were measured: (1) heading day (the day on which a plant has three emerged panicles); (2) flag leaf height (the flag leaf is the highest leaf on a grass stem); (3) flag leaf blade length; (4) flag leaf blade width; (5) panicle length; (6) tiller leaf width; (7) tiller leaf length; (8) first internode length; and (10) plant height.

The trial consisted of commercially available cultivars and the BE9301A variety. Tables 2-3 show comparisons of several morphological characteristics of the BE9301A variety with other tall fescue varieties.

TABLE 2

Morphological characteristics in 2004 Data Collection year 2004

| Variety Name | Heading Day Julian | Flag Leaf Height cm | Flag Leaf Length cm | Flag Leaf Width mm | Panicle Length cm | Tiller Leaf Width mm | Tiller Leaf Length cm | First Internode Length cm | Plant Height cm |
|---|---|---|---|---|---|---|---|---|---|
| BAR 3FA BTR9 | 162.1 a | 54.2 e | 19.8 a | 7.3 | 28.2 ab | 9.2 | 27.4 abc | 17.4 ef | 106.1 d |
| Barianne | 160.6 a | 60.7 a-d | 18.6 a | 7.7 | 30.9 a | 10.7 | 27.8 a | 20.1 cde | 112 cd |
| BAR FA 1BTR10 | 157.8 ab | 53.1 e | 18.4 a | 8.6 | 28.3 ab | 10.6 | 26 a-e | 18.2 def | 111.8 cd |
| Barcel | 157.8 ab | 55.8 de | 19.7 a | 8.4 | 28.3 ab | 10.3 | 27.2 a-d | 19.1 def | 115.6 a-d |
| BE9301 A | 157.3 abc | 55.8 de | 19.3 a | 8.4 | 28.5 ab | 11.1 | 28.3 a | 20.7 bcd | 122.1 ab |
| Barolex | 156.9 abc | 52.2 e | 19.3 a | 7.4 | 27.6 b | 9.3 | 27.7 ab | 17 f | 113.1 bcd |
| Kentucky 31+ | 154.4 bcd | 65 a | 13.5 cd | 7.9 | 28.6 ab | 11.7 | 22.9 fg | 23.9 a | 121.7 abc |
| Barcarella | 153.6 b-e | 64.7 ab | 15.3 bc | 7.6 | 27.4 bc | 10.1 | 23.4 ef | 24.2 a | 119.4 abc |
| Kentucky 31− | 151.4 cde | 59.8 bcd | 12.7 d | 7.5 | 27.8 b | 10.6 | 20.3 g | 22.1 abc | 120.9 abc |
| BTR 6 | 150.5 def | 64.7 ab | 16 b | 7.7 | 28.7 ab | 10.9 | 24.5 c-f | 23.4 ab | 125.5 a |
| Dovey | 148.3 efg | 57.1 cde | 15.2 bc | 7.3 | 26.3 bcd | 10.5 | 24.2 def | 23.8 a | 117.5 abc |
| Forager | 147.6 efg | 60.3 a-d | 15.8 bc | 7.1 | 24.6 cd | 10.2 | 27.9 a | 24.8 a | 112.8 bcd |
| Bar Fa 6FRD | 145.3 fg | 57 cde | 15.3 bc | 7.4 | 26.5 bcd | 10 | 24.7 b-f | 23 ab | 120.6 abc |
| Fawn | 142.5 g | 62 abc | 13.8 bcd | 6.4 | 23.7 d | 9.1 | 24.8 b-f | 22.9 abc | 113.2 bcd |
| LSD (P = .05) | 6.12 | 4.94 | 2.44 | NS | 2.83 | NS | 3.03 | 2.79 | 10.02 |
| CV | 2.38 | 5.01 | 8.76 | 9.6 | 6.12 | 10.26 | 7.07 | 7.75 | 5.12 |

Means followed by same letter do not significantly differ (P = .05, LSD)
NS = Non Significant

TABLE 3

Morphological characteristics in 2005 Morphological measurements in various forage tall fescue cultivars
Trial ID: 03-Fa-Morph
Location: Albany
Data Collection year: 2005

| Variety Name | Heading Day Julian | Flag Leaf Height cm | Flag Leaf Length cm | Flag Leaf Width mm | Panicle Length cm | Tiller Leaf Width mm | Tiller Leaf Length cm | First Internode Length cm | Plant Height cm |
|---|---|---|---|---|---|---|---|---|---|
| Barianne | 129.8 a | 82.8 a-d | 27.3 a | 7.5 | 35.4 a | 8.5 b-e | 38.6 ab | 54.7 | 133.2 |
| BTR 10 | 126 ab | 76.9 cde | 25 ab | 7.2 | 29.4 bc | 9.2 bcd | 35.4 bcd | 57.6 | 128.5 |
| BTR 9 | 124.8 bc | 76.6 de | 24.5 bc | 7.1 | 28.8 b-e | 8.4 b-e | 43.2 a | 51.4 | 124.3 |
| Barolex | 123.5 bcd | 78.2 cde | 22.2 cd | 6.5 | 29.9 bc | 7.6 def | 35 bcd | 55.7 | 129.2 |
| Barcel | 122.8 bcd | 74.4 de | 24.1 bc | 6.2 | 30.2 bb-e | 7.5 def | 35.2 bcd | 51.9 | 124.4 |
| BE9301 A | 122 cd | 80.1 bcd | 24.1 bc | 6.7 | 28.8 | 8.1 b-f | 36.5 abc | 55.3 | 131.2 |
| Barcarella | 121.5 cd | 90.2 abc | 19.1 efg | 6.5 | 28.8 b-e | 9.8 abc | 29.9 c-f | 49 | 126.9 |
| BTR 6 | 120.7 d | 85.2 a-d | 22.7 bcd | 8.5 | 30 bc | 8.4 b-e | 35.3 bcd | 52.6 | 135.8 |
| K31+ | 116.7 e | 95.7 a | 20.5 def | 8.2 | 31.5 b | 9.9 ab | 30.7 c-f | 57 | 145.2 |
| Bar Fa 6FRD | 114 e | 80.8 bcd | 22.7 bcd | 7.3 | 30.1 bc | 11.2 a | 33.7 b-e | 54.5 | 125.2 |
| K31− | 113.8 e | 91.5 ab | 21.2 de | 6.9 | 29.2 bcd | 8 c-f | 28.1 d-g | 57.4 | 140.2 |
| Forager | 106.3 f | 65.9 e | 15.6 h | 5.3 | 25.5 e | 6.9 ef | 22.2 g | 56.3 | 120.9 |
| Fawn | 103.3 f | 75.7 de | 17.8 gh | 6.9 | 26.7 cde | 6.4 f | 26.4 efg | 56.1 | 128.1 |
| Dovey | 97.6 g | 76.1 de | 17.9 fgh | 6.3 | 25.8 de | 8.1 b-f | 23.2 fg | 58.3 | 147.7 |
| LSD (P = .05) | 3.95 | 13.31 | 2.65 | NS | 3.49 | 1.88 | 7.74 | NS | NS |
| CV | 2.01 | 9.82 | 7.24 | 14.53 | 7.09 | 13.3 | 14.24 | 6.61 | 9.68 |

Means followed by same letter do not significantly differ (P = .05, LSD)
NS = Non Significant Table 4 provides a summary of the analysis of persistence for tall fescue, perennial ryegrass and Kentucky bluegrass varieties. Grasses were sown in September 2002 in Princeton, Ky., and persistence analyzed on the dates shown in the Table.

TABLE 4

Percent stand of tall fescue, perennial ryegrass (PRG) and Kentucky bluegrass (BG) varieties sown Sep. 25, 2002 in a cattle grazing tolerance study at Princeton, Kentucky.

| | Percent Stand | | | | | |
|---|---|---|---|---|---|---|
| | 2003 | | 2004 | | 2005 | |
| Variety | Apr 3 | Dec 2 | Apr 1 | Dec 21 | Apr 15 | Nov 3 |
| Commercial Varieties--Available for Farm Use | | | | | | |
| Select | 90 | 78 | 77 | 78 | 68 | 83* |
| KY31+[1] | 90 | 78 | 78 | 75 | 72 | 81* |
| Festival | 90 | 76 | 75 | 80 | 72 | 78* |
| Calibra (PRG) | 90 | 85 | 79 | 67 | 72 | 37 |
| Certified Kenblue (BG) | 90 | 23 | 25 | 25 | 33 | 33 |
| Experimental Varieties | | | | | | |
| FA 2845 | 90 | 80 | 84 | 80 | 78 | 87* |
| KYFA9301 | 90 | 79 | 78 | 80 | 77 | 83* |
| KYFA9304 | 90 | 79 | 78 | 80 | 78 | 83* |
| AGRFA 104 | 90 | 78 | 80 | 77 | 77 | 82* |
| AGRFA 106 | 90 | 77 | 78 | 75 | 78 | 82* |
| AGRFA 114 | 90 | 78 | 78 | 85 | 73 | 82* |
| KY31-[1] | 90 | 81 | 79 | 78 | 72 | 81* |
| FA 2458 | 90 | 75 | 77 | 77 | 73 | 78* |
| FA 2651 | 90 | 77 | 76 | 75 | 72 | 78* |
| FA 2720 | 90 | 78 | 80 | 80 | 73 | 77* |
| BE9301A | 90 | 78 | 78 | 75 | 72 | 77* |
| HM11 | 90 | 75 | 70 | 80 | 77 | 72 |
| AGRFA 111 | 90 | 70 | 73 | 67 | 68 | 62 |
| EC411 (PRG) | 90 | 83 | 84 | 77 | 70 | 53 |
| KYPP 9901 (BG) | 86 | 12 | 26 | 28 | 33 | 40 |
| HB96 (BG) | 6 | 13 | 5 | 10 | 18 | 22 |
| HB95 (BG) | 5 | 10 | 13 | 15 | 18 | 17 |
| Mean | 83 | 68 | 67 | 67 | 65 | 68 |
| CV, % | 2 | 11 | 12 | 12 | 15 | 15 |
| LSD, 0.05 | 2 | 9 | 9 | 9 | 11 | 11 |

*Not significantly different from the highest value in the column, based on the 0.05 LSD.
[1]"+" indicates variety is endophyte infected; "−" indicates variety is endophyte free.

EXAMPLE 6

Resistance to Rust and Bacterial Wilt

The susceptibility of BE9301A tall fescue to rust (Stem rust, *Puccinia grammis*) and bacterial wilt (*Xanthomonas* spp) was measured. Seeds were grown as described in Example 5. Symptoms of a rust disease and bacterial wilt (which occurred naturally) were visible. Initial symptoms of rust were visible damage of leaves by rust spores, and there were also brown stripes visible on the leaves.

Differences in rust and bacterial wilt susceptibility were observed for BE9301A, which was superior to other known cultivars.

EXAMPLE 7

Alkaloids Characterization

This example describes methods used to characterize the amount of alkaloids (such as ergovaline) present in BE9301A grass.

Endophytic funguses can produce alkaloids. Of the alkaloids produced ergovaline can cause animal health problems at certain concentrations. Toxicosis due to ergovaline is induced in livestock at the following concentrations: horses, 300-500 ppb (0.3-0.5 ppm); cattle, 400-750 ppb (0.4-0.75 ppm); and sheep, 88-1200+ ppb (0.8-1.2 ppm). Therefore, BE9301A grass samples and seed were analyzed for the presence of alkaloids.

The presence of ergovaline was determined using chromatogram analysis. Experimentation was performed by the Oregon State University College of Veterinary Medicine. To detect ergovaline alkaloid, fluorometric HPLC assays were conducted. BE9301A and other grasses (BAR FA 1004, Kentucky 31+ and Kentucky 31−) were grown in Lexington, Ky. Samples were oven-dried and then analyzed. Fescue straw was analyzed as a control. As shown in Table 5, BE9301A grass plants were found to have about 27-56 ppb of ergovaline. This indicates that the levels of ergovaline in BE9301A hay are safe for animal consumption.

TABLE 5

Alkaloids in BE9301A*

| Sample | Sample collected May 3, 2002, reported Jun. 19, 2002 | Sample collected Jul. 24, 2002, reported Aug. 28, 2002 | Sample collected Oct. 22, 2002, reported Nov. 18, 2002 |
|---|---|---|---|
| | Ergovaline | Ergovaline | Ergovaline |
| BAR FA 1004 | <10 | <10 | <10 |
| BE 9301A | 38 | 27 | 56 |
| *Kentucky 31+ | 524 | 307 | 792 |
| *Kentucky 31− | <10 | <10 | <10 | amounts of ergovaline in ppb
Samples noted as "+" include endophyte and samples notes as "−" do not include endophyte BE9301A and other tall fescues grown in Mas Grenier, France were analyzed for the presence of ergovaline using HPLC with fluorimetric detection from an adaptation of the method of Hill et al. (*Crop Science* 33:331-3, 1993). Grass was grown in 2002. As shown in Table 6, BE9301A grass had about 0.05-0.12 ppm of ergovaline, which is significantly less than the toxic tall fescue Kentucky 31+.

TABLE 6

Amount of ergovaline present in tall fescues growing in Mas Grenier.

| Variety | Ergovaline µg/g (ppm) | % Endophytes in plot | Ergovaline ug/g with 100% E+ | Ergotamine ug/g with 100% E+ |
|---|---|---|---|---|
| Cut 21 Jun. 2002 | | | | |
| BE9301A | 0.12 | 53.30% | 0.225 | 0.169 |
| Kentucky 31+ | 0.27 | 36.60% | 0.737 | 0.205 |
| Cut 26 Sep. 2002 | | | | |
| BE9301A | 0.12 | 53.30% | 0.225 | 0.182 |
| Kentucky 31+ | 0.22 | 36.60% | 0.601 | 0.273 |
| Cut 13 Nov. 2002 | | | | |
| BE9301A | 0.05 | 53.30% | 0.093 | |
| Kentucky 31+ | 0.10 | 36.60% | 0.273 | |

Tall fescues including BE9301A were grown in Lexington, Ky. Forage clipping samples were obtained and freeze dried, then analyzed for the presence of ergovaline and a complex of all ergot alkaloids that are considered harmful to animals. (ELISA test, Agrinostics Ltd., developed by Dr. Nick Hill, University of Georgia). As shown in Table 7, BE9301A contains an average of about 98-309 ppb alkaloid, less than Kentucky 31 (KY31+), indicating it is safe for animal consumption.

TABLE 7

Comparison of alkaloids in tall fescues.

| | | Samples collected Aug. 15, 2003, reported on Sep. 14, 2003 ppb alkaloid | | | Sample collected Nov. 18, 2003, |
|---|---|---|---|---|---|
| Variety | Rep | ELISA 1 | ELISA 2 | AVE | ppb alkaloid |
| Barolex | 1 | 7 | 0 | 3 | 603 |
| Barolex | 2 | 4 | 0 | 2 | |
| Kentucky31+ | 1 | 1249 | 1182 | 1216 | 2235 |
| Kentucky31+ | 2 | 1532 | 1509 | 1521 | |
| BE9301A | 1 | 100 | 98 | 99 | |
| BE9301A | 2 | 136 | 152 | 144 | 309 |

This data indicates that BE9301A grass plants and straw are safe for livestock. Therefore, BE9301A straw and grass plants can be used in pastures for grazing, and to make hay to feed to livestock.

Figure 1A:
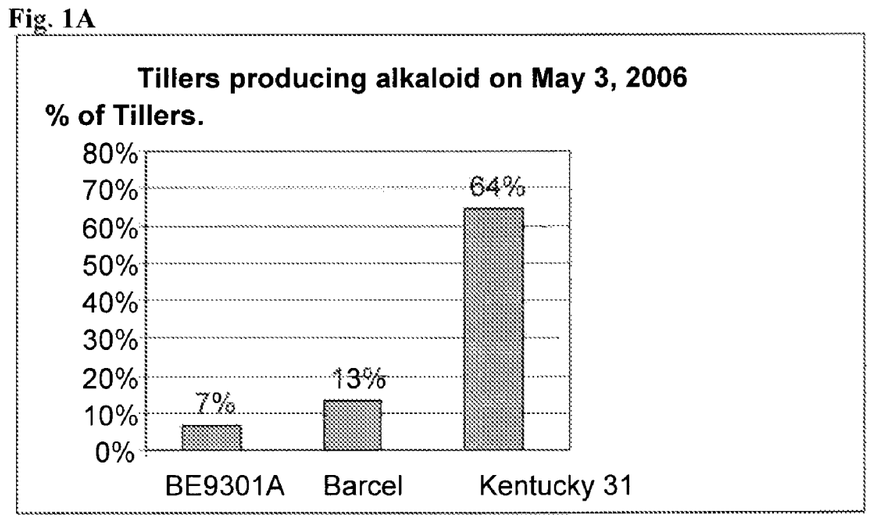
FIGS. 1A-1C show the % of tillers producing alkaloids from three fescue varieties on May 3, 2006 (FIG. 1A), Jan. 12, 2007 (FIG. 1B), and Feb. 28, 2007 (FIG. 1C).
Figure 1B:
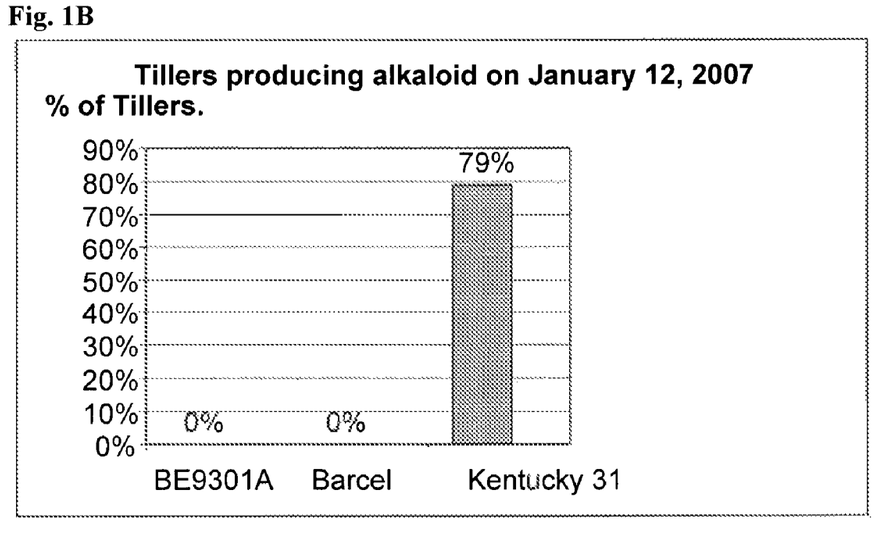
Figure 1C:
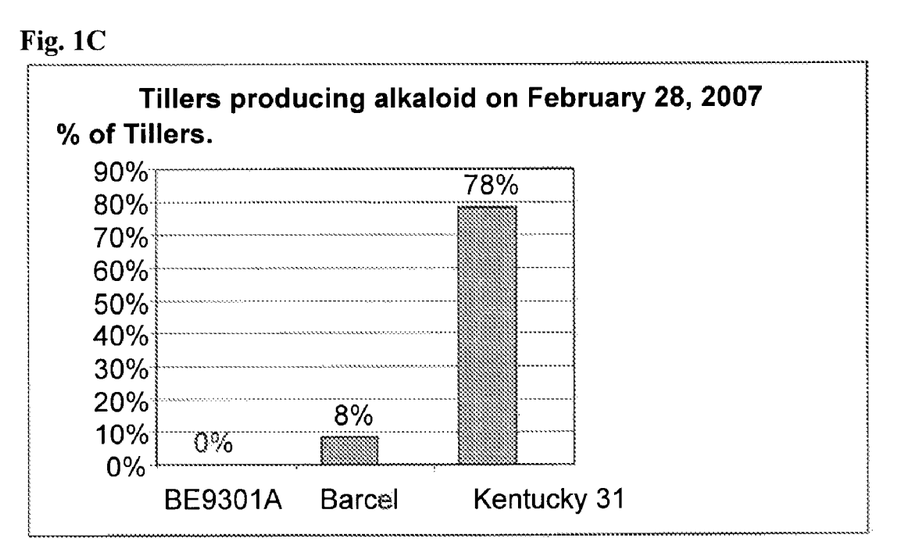

Additional data was collected in 2006 and 2007, further indicates that BE9301A produces low levels of alkaloids (see, FIGS. 1A-1C).

EXAMPLE 8

Grazing Trial

This example describes methods used to demonstrate that BE9301A is not toxic to livestock, is persistent in pastures, and is acceptable to cattle. The data in example 7 indicate that BE9301A is safe for animal consumption. However, endophytes produce many alkaloids besides ergovaline whose effects are not clearly understood. Therefore these grazing and feeding trial methods were used to validate the safety and productivity of an inoculated endophyte grass combination.

Animal grazing trials were performed as follows. Varieties Kentucky 31 (KY31+), BE9301A, and Barcel (see Example 1) were sown in October 2004 in Hope, Ark., with three replications. Each replication was a two acre pasture. In the spring-summer 2006 and 2007, each pasture was stocked with six calves, for two grazing seasons (2 years from mid-January to early June).

As shown in Tables 8 and 9, in 2006, the Average Daily Weight gain (ADG) was significantly higher for BE9301A compared to the toxic Kentucky 31. In 2007, and the total gain/calf in BE9301A pasture is significantly higher than Kentucky 31 and Barcel.

TABLE 8

Performance of steers grazing native infected endophyte (Kentucky 31), endophyte free (Barcel), or novel endophyte infected tall fescue (BE9301A) during the 2006 production year.

| Date | Kentuky-31 | Barcel | BE 9301A | SE |
|---|---|---|---|---|
| Body Weight, lb | | | | |
| January 4 | 503 | 503 | 500 | 14.74 |
| February 1 | 568 | 603 | 588 | 17.92 |
| March 1 | 610 | 674 | 637 | 17.21 |
| March 29 | 642 | 734 | 694 | 23.8 |
| April 26 | 690$^a$ | 822$^b$ | 780$^b$ | 22.57 |
| May 24 | 683$^a$ | 828$^b$ | 798$^b$ | 23.63 |
| June 21 | 719$^a$ | — | 824$^b$ | 23.63 |
| Average Daily Gain, lb | | | | |
| Jan. 4 to Feb. 1 | 2.30 | 3.57 | 3.11 | 0.35 |
| Feb. 1 to Mar. 1 | 1.48 | 2.51 | 1.76 | 0.30 |
| Mar. 1 to Mar. 29 | 1.15 | 2.17 | 2.04 | 0.35 |
| Mar. 29 to Apr. 26 | 1.71$^a$ | 3.13$^c$ | 3.07$^{bc}$ | 0.20 |
| Apr. 26 to May 24 | −0.25 | 0.21 | 0.63 | 0.56 |
| May 24 to Jun. 21 | 1.34 | — | 0.93 | 0.26 |
| Overall ADG | 1.29$^a$ | 2.32$^{cd}$ | 1.93$^{bc}$ | 0.13 |
| Total Gain/calf, lb | 213$^a$ | 325$^b$ | 324$^b$ | 24.8 |
| Grazing-d/acre | 275$^{bc}$ | 227$^a$ | 252$^{ab}$ | 9.8 |
| Gain/acre, lb | 331$^a$ | 512$^b$ | 485$^b$ | 43.5 |

$^{abcd}$Least-square means with uncommon superscripts differ (p ≦ 5)
SE: Standard Error of mean Similar grazing trials were performed in 2007 and the results are shown in Table 9, below.

TABLE 9

Performance of steers grazing native infected endophyte (Kentucky 31), endophyte free (Barcel), ArkPlus, or novel endophyte (BE9301A) infected tall fescue during the 2007 production year.

| | KY-31 | Barcel | BE9301A | SE |
|---|---|---|---|---|
| Body Weight, lb | | | | |
| January 9 | 583 | 580 | 572 | 44.5 |
| February 6 | 612 | 631 | 617 | 44.1 |
| March 6 | 654 | 676 | 666 | 33.6 |
| April 3 | 687 | 724 | 723 | 29.6 |
| May 1 | 730 | 748 | 793 | 53.2 |
| May 29 | — | — | 826 | 55.7 |
| Average Daily Gain, lb | | | | |
| Jan. 9 to Feb. 6 | 1.03 | 1.82 | 1.62 | 0.22 |
| Feb. 6 to Mar. 6 | 1.36 | 1.33 | 1.65 | 0.41 |
| Mar. 6 to Apr. 3 | 1.18 | 2.36 | 2.05 | 0.54 |

TABLE 9-continued

Performance of steers grazing native infected endophyte (Kentucky 31), endophyte free (Barcel), ArkPlus, or novel endophyte (BE9301A) infected tall fescue during the 2007 production year.

|  | KY-31 | Barcel | BE9301A | SE |
|---|---|---|---|---|
| Apr. 3 to May 1 | 1.55 | 0.86 | 2.43 | 0.49 |
| May 1 to May 29 | — | — | 1.17 | 0.58 |
| Overall ADG | 1.24 | 1.67 | 1.80 | 0.18 |
| Total Gain/calf, lb | 131[a] | 94[a] | 236[b] | 35.9 |
| Grazing-d/acre[1] | 154[bc] | 84[a] | 196[c] | 24.0 |
| Gain/acre, lb | 196[a] | 140[a] | 354[b] | 53.9 |

[1]Calves were removed from 2 Barcel, 1 KY-31, and 1 BAR FA BE 9301A pasture due to flooding, cattle were subsequently returned to 1 Barcel, the KY-31, the BAR FA BE 9301A, pasture. The trial was ended for 1 Barcel pasture on 6 February, and 1 Barcel pasture on 6 March, because of low stand counts and forage availability.
[a-c]Least-squares means with differing superscripts differ (P < 0.08).
SE: Standard Error of mean At various times since the grazing trial was established, stand density of the pastures was calculated by conducting stand counts at 20 places in each pasture. The average percent stand density for all pastures of a given variety are shown in Table 10, below. While BE9301A provided better weight gains than Kentucky 31 and Barcel; its persistence was good as the stand density of BE9301A did not decline during the length of the grazing trial. The stand density of endophyte free Barcel was drastically reduced, indicating that BE9301A with endophyte E-34 has better stand persistence.

TABLE 10

Stand Density of indicated varieties.

|  | December 2005 | May 2006 | January 2007 | 1 Mar. 2007 | 4 May 2007 |
|---|---|---|---|---|---|
| Kentucky31+ | 89% | 86% | 80% | 85% | 85% |
| BE9301A | 68% | 69% | 64% | 59% | 61% |
| Barcel | 45% | 32% | 19% | 10% | 13% |

Animal behavior observations were also conducted in the grazing trial. Cattle were monitored daily from January 2006 to May 2006, and the percent of the day that they spent grazing, cooling in the shade, or sunning was recorded. Cattle that were in the BE9301A pastures spent significantly more time grazing compared to Kentucky 31 during the middle of the day. The cattle on Kentucky 31 pastures were standing in shade. This shows the classical symptom of the Kentucky 31 endophyte toxicity where the cattle is heat-stressed and spends more time cooling off rather than grazing resulting in loss of productivity. Cattle on BE9301A pastures did not show such behaviors of toxicity. Thus, this indicates that the endophyte E-34 in BE9301A does not have toxic symptoms like the endophyte in Kentucky 31.

The animal weight gains; stand persistence data; and behavioral data indicate that BE9301A grass is useful, inter alia, as a pasture grass.

EXAMPLE 9

Production of BE9301A Grasses

BE9301A can be grown under normal conditions for growing turf grasses, and bulk seed for large-scale planting can be obtained by methods known in certified seed production. For example, bulk seed may be produced by planting BE9301A seeds and allowing the mature plants to produce seed by cross-pollination with each other and then collecting the seed. Standard precautions should be taken to prevent cross-pollination from other grasses, such as growing the variety in an isolated plot of sterilized soil, removing adjacent vegetation, and so forth. The BE9301A seeds deposited with ATCC are breeder seeds; propagation of plants from these seeds can be performed under standard conditions known to those skilled in the art.

EXAMPLE 10

Exemplary Uses of BE9301A

BE9301A can be used in the same way as other tall fescue varieties. However, the increased palatability and late maturing date of this grass affords BE9301A particular advantages over other varieties. Therefore, this grass and seed can be used in areas where high forage quality grass for animals is desired, for example on a farm, in a pasture, or for hay production. Thus, BE9301A is especially marketable and therefore useful.

EXAMPLE 11

Introducing Traits of BE9301A into Other Grass Varieties

The morphological and physiological characteristics of BE9301A, including increased digestibility, palatability, decreased toxicity, later maturing date, or combinations thereof, can be introduced into other grass varieties (such as other forage grasses) by conventional breeding techniques. For example, BE9301A can be grown in pollination proximity to another variety of tall fescue grass, allowing cross-pollination to occur between BE9301A and the other variety, and then harvesting the hybrid seeds. Plants grown from these hybrid seeds can then be tested for the maintenance of the molecular characteristics described above for BE9301A, and/or the plants can simply be observed to see if they display the same growth characteristics described in the above tables. Ideally, the hybrid plants and seeds retain the E34 endophyte.

For example, plants grown from these hybrid seeds can be tested for any of the morphological characteristics described herein, for the presence of the endophyte, for lower amounts of alkaloids (for example as compared to Kentucky 31), or combinations thereof. In this way, these desirable characteristics can be combined with other desirable plant characteristics. Thus, the provision of BE9301A enables the production of progeny plants of BE9301A having the desired characteristics for grazing animals (such as increased palatability). "Progeny plants" of BE9301A are any plants that are the offspring of a cross between BE9301A and any other plant or plants. Progeny plants also include successive generations of the offspring, for example those selected for the desired BE9301A characteristics using the methods described herein. First-generation progeny plants may retain the desired characteristics of the BE9301A parent. However, if a first-generation progeny plant does not retain the desired level of digestibility and palatability (or alkaloid levels) observed with BE9301A, subsequent generations of offspring can be recycled for digestibility and palatability (or alkaloid levels) which have at least the same digestibility and palatability and alkaloid characteristics of BE9301A described herein. In one example, subsequent generations of offspring can have alkaloid levels below that of BE9301A or have better digestibility and palatability than BE9301A.

In addition, BE9301A can be used as transformation targets for the production of transgenic grasses. In certain examples, the present disclosure contemplates the transformation of cells derived from BE9301A with at least one transgene. For example, transgenes that can be used, include, but are not limited to, transgenes that confer resistance to herbicides (such as, but not limited to glyphosate), insect, disease (viral, bacterial, fungal, nematode) or drought resistance, standability, prolificacy, salt damage resistance, and quality are useful. Examples of such genes and methods of transforming plants are described in U.S. Pat. No. 6,025,545 (Lundquist et al.).

EXAMPLE 12

Inoculation of Other Grasses with Endophyte

The E34 endophyte can also be used to inoculate other grasses, such as forage perennial ryegrass. Such synthetic combinations of endophyte and grass or endophyte and seed can be used for grazing or for planting in a pasture. For example, the inoculation methods described in Example 1 can be used to inoculate seeds from any desired grass, such as a forage grass (such as those listed in the summary section).

EXAMPLE 13

Forage Yield and Palatability

This example provides results indicating that BE9301A has acceptable forage yield and palatability. The trial was conducted in Mas Grenier, France. Palatability measured through sheep preference trials. Briefly, sheep were given the opportunity to graze on the varieties described below and their preferences were recorded using standard methodology. The results indicate that the forage yield and palatability of BE9301A is higher than Kentucky 31+.

TABLE 11

Forage Yield and Palatability of BE9301A.

| Variety | Forage Yield (% of average) | Palatability (1 = worst; 9 = best) |
| --- | --- | --- |
| BarElite | 94 | 7.5 |
| Barolex | 94 | 6.2 |
| BE9301A | 105 | 5.8 |
| Kentucky 31+ | 92 | 4.7 |
| BAR FA 9BTR6 | 106 | 2.3 |
| cv. | 3 | 4 |
| LSD (.05) | 9 | 0.5 |

Forage Yield: Average of 8 cuttings in 2006 and 2007
Palatability: Average of 7 observations in 2006 and 2007

Cell wall digestibility measured by NIRS (Near infrared reflectance spectroscopy). The samples were collected from two year old tall fescue trial grown in Crossville, Ala. The samples used for forage quality analysis are from the first cutting in 2006. The data indicates that BE9301A has better digestibility than Kentucky 31.

TABLE 12

Cell Wall digestibility of BE9301A

| Variety | % CWD |
| --- | --- |
| BarElite | 52.3 |
| BE 9301A | 48.9 |
| Barolex | 48.9 |
| BAR FA 9BTR 6 | 47.8 |

TABLE 12-continued

Cell Wall digestibility of BE9301A

| Variety | % CWD |
| --- | --- |
| Kentucky 31+ | 46.4 |
| Kentucky 31− | 44.9 |
| LSD (P = .05) | 2.76 |
| CV | 3.55 |

EXAMPLE 14

Genetic Engineering of Endophyte E34

The endophyte provided herein can be used as a host for the introduction or deletion of various nucleic acid sequences (for example through the use of recombinant nucleic acid sequences). For example, the genes responsible for alkaloid biosynthesis can be attenuated through deletion or alteration of their control sequences using the methods described in U.S. Pat. No. 6,335,188, which is herein incorporated by reference.

In view of the many possible embodiments to which the principles of the disclosed invention can be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

We claim:

1. An isolated endophyte from grass seed deposited as ATCC No: PTA-7709, wherein the isolated endophyte consists of an endophyte deposited under Centraalbureau voor Schimmelcultures Deposit No. CBS 119998.

2. The isolated endophyte from the grass seed deposited of claim 1, wherein the seed comprises about 10-100 ppb of ergovaline.

3. An axenic culture of an endophyte deposited under Centraalbureau voor Schimmelcultures Deposit No. CBS 119998.

4. A synthetic combination of the endophyte of claim 3 with a grass plant or grass cultivar, wherein the grass plant or grass cultivar is a tall fescue or a perennial ryegrass.

5. The synthetic combination of claim 4, which has been made by inoculating the grass plant or grass cultivar with the axenic culture of the endophyte.

6. The synthetic combination of claim 4, which has been made by crossing the synthetic endophyte/grass plant or grass cultivar combination with an endophyte-free grass plant or grass cultivar to form a new grass plant or grass cultivar infected with the endophyte.

7. Seeds of the synthetic combination of claim 4, wherein said seeds comprise the endophyte deposited under Centraalbureau voor Schimmelcultures Deposit No. CBS 119998.

8. The seeds of claim 7, wherein the seeds have been harvested from grass plants inoculated with the endophyte.

9. The seeds of claim 7, wherein the seeds have been harvested from:
plants of the synthetic endophytes/grass plant or grass cultivar combination grown from seeds harvested from grass plants inoculated with the endophyte, or
from seeds of subsequent generations of grass plants inoculated with the endophyte.

10. The endophyte of claim 3, further comprising a recombinant nucleic acid sequence.

11. The synthetic combination of claim 4, wherein the grass plant or grass cultivar is a tall fescue.

12. The synthetic combination of claim 11, wherein the tall fescue is Dovey, Drover, Prosper, Barcarella, BAR FA 6FRD, Barcel, Barolex, BarElite, or Bariane.

13. The synthetic combination of claim 11, wherein the tall fescue is BE9301A.

14. The synthetic combination of claim 4, wherein the grass plant or grass cultivar is a perennial ryegrass.

15. The synthetic combination of claim 14, wherein the perennial ryegrass is Barsprinter or Remington.

16. A synthetic combination of the endophyte of claim 1 with a grass plant or grass cultivar, wherein the grass plant or grass cultivar is a tall fescue or a perennial ryegrass.

17. The synthetic combination of claim 16, wherein the grass plant or grass cultivar is a tall fescue.

18. The synthetic combination of claim 17, wherein the tall fescue is Dovey, Drover, Prosper, Barcarella, BAR FA 6FRD, Barcel, Barolex, BarElite, or Bariane.

19. The synthetic combination of claim 17, wherein the tall fescue is BE9301A.

20. The synthetic combination of claim 16, wherein the grass plant or grass cultivar is a perennial ryegrass.

21. The synthetic combination of claim 20, wherein the perennial ryegrass is Barsprinter or Remington.

22. The synthetic combination of claim 16, which has been made by inoculating the grass plant or grass cultivar with the isolated endophyte.

23. The synthetic combination of claim 16, which has been made by crossing the synthetic endophyte/grass plant or grass cultivar combination with an endophyte-free grass plant or grass cultivar to form a new grass plant or grass cultivar infected with the endophyte.

24. Seeds of the synthetic combination of claim 16, wherein said seeds comprise the endophyte deposited under Centraalbureau voor Schimmelcultures Deposit No. CBS 119998.

25. The seeds of claim 24, wherein the seeds have been harvested from grass plants inoculated with the endophyte.

26. The seeds of claim 24, wherein the seeds have been harvested from:
plants of the synthetic endophytes/grass cultivar combination grown from seeds harvested from grass plants inoculated with the endophyte, or
from seeds of subsequent generations of grass plants inoculated with the endophyte.

27. The isolated endophyte of claim 1, further comprising a recombinant nucleic acid sequence.

28. A tall fescue grass plant comprising the endophyte of claim 1.

29. The tall fescue grass plant claim 28, wherein the tall fescue is Dovey, Drover, Prosper, Barcarella, BAR FA 6FRD, Barcel, Barolex, BarElite, or Bariane.

30. The tall fescue grass plant of claim 28, wherein the tall fescue is BE9301A.

31. A perennial ryegrass plant comprising the endophyte of claim 1.

32. The perennial ryegrass plant of claim 31, wherein the perennial ryegrass plant is Barsprinter or Remington.

33. A tall fescue grass plant comprising the endophyte of claim 3.

34. The tall fescue grass plant claim 33, wherein the tall fescue is Dovey, Drover, Prosper, Barcarella, BAR FA 6FRD, Barcel, Barolex, BarElite, or Bariane.

35. The tall fescue grass plant of claim 33, wherein the tall fescue is BE9301A.

36. A perennial ryegrass plant comprising the endophyte of claim 3.

37. The perennial ryegrass plant of claim 36 wherein the perennial ryegrass plant is Barsprinter or Remington.

* * * * *

UNITED STATES PATENT AND TRADEMARK OFFICE
CERTIFICATE OF CORRECTION

PATENT NO. : 7,642,424 B2
APPLICATION NO. : 11/775702
DATED : January 5, 2010
INVENTOR(S) : Van Hanja et al.

It is certified that error appears in the above-identified patent and that said Letters Patent is hereby corrected as shown below:

In the Specification:

Column 10, in Table 3, under the column entitled "Panicle Length cm," the fifth entry, "30.2 bb-e" should be --30.2 b--.

Column 10, in Table 3, under the column entitled "Panicle Length cm," the sixth entry "28.8" should be --28.8 b-e--.

Signed and Sealed this

Thirteenth Day of April, 2010

David J. Kappos
*Director of the United States Patent and Trademark Office*